(12) United States Patent
Tanaka

(10) Patent No.: US 8,777,345 B2
(45) Date of Patent: Jul. 15, 2014

(54) BRONZING INDEX VALUE CALCULATION METHOD, BRONZING INDEX VALUE CALCULATION DEVICE, AND PRINTING DEVICE

(75) Inventor: Katsuyuki Tanaka, Fujimi-machi (JP)

(73) Assignee: Seiko Epson Corporation, Tokyo (JP)

( * ) Notice: Subject to any disclaimer, the term of this patent is extended or adjusted under 35 U.S.C. 154(b) by 258 days.

(21) Appl. No.: 13/435,843

(22) Filed: Mar. 30, 2012

(65) Prior Publication Data

US 2012/0249633 A1    Oct. 4, 2012

(30) Foreign Application Priority Data

Apr. 1, 2011  (JP) ................................ 2011-081714
Jun. 15, 2011  (JP) ................................ 2011-132808

(51) Int. Cl.
  *B41J 29/38*  (2006.01)
  *B41J 29/393*  (2006.01)
(52) U.S. Cl.
  USPC .................................... 347/9; 347/16; 347/19
(58) Field of Classification Search
  USPC .................................................. 347/9, 16, 19
  See application file for complete search history.

(56) References Cited

U.S. PATENT DOCUMENTS

2004/0008244 A1*  1/2004  Tsujimoto ..................... 347/105
2005/0073544 A1*  4/2005  Scofield et al. ................. 347/16
2005/0094871 A1  5/2005  Berns et al.
2006/0285742 A1  12/2006  Arai et al.
2007/0243314 A1  10/2007  Jinno
2010/0055424 A1  3/2010  Yoshida et al.

FOREIGN PATENT DOCUMENTS

| JP | 2004-276521 A | 10/2004 |
| JP | 2005-194500 A | 7/2005 |
| JP | 2005-274340 A | 10/2005 |
| JP | 2006-297780 A | 11/2006 |
| JP | 2007-511161 A | 4/2007 |
| JP | 2007-511175 A | 4/2007 |
| JP | 2007-288270 A | 11/2007 |
| JP | 2009-160802 A | 7/2009 |
| JP | 2010-052247 A | 3/2010 |
| JP | 2010-147586 A | 7/2010 |
| JP | 2010-166202 A | 7/2010 |
| JP | 2011-077974 A | 4/2011 |
| JP | 2011-077975 A | 4/2011 |

* cited by examiner

*Primary Examiner* — Jason Uhlenhake
(74) *Attorney, Agent, or Firm* — Global IP Counselors, LLP

(57) ABSTRACT

Calculating a difference between a hue angle of a colorimetric value of a printed object with respect to diffuse reflection and the hue angle of a colorimetric value of the printed object with respect to specular reflection, calculating the difference between a standard chroma with respect to an observational light source and the chroma of the colorimetric value of the printed object with respect to specular reflection under the observational light source, and calculating a bronzing index value on the basis of a value obtained by multiplying the calculated difference of the hue angles by the calculated difference of the chromas.

5 Claims, 15 Drawing Sheets

| Category of Sheet Paper | Gradation Value | Ij | | | |
|---|---|---|---|---|---|
| | | C | M | Y | K |
| Plain Paper | 1<br>2<br>·<br>·<br>·<br>255 | 0.1<br>0.1 | ·<br>·<br>·<br>· | ·<br>·<br>·<br>· | |
| Cardboard | 1<br>2<br>·<br>·<br>·<br>255 | ·<br>·<br>·<br>·<br>· | ·<br>· | · | · |
| Coated Paper | 1<br>2<br>·<br>·<br>·<br>255 | | · | · | · |
| Special Paper | 1<br>2<br>·<br>·<br>·<br>255 | ·<br>·<br>·<br>·<br>·<br>0.8 | ·<br>· | · | 0.9 |

Fig. 8

COLOR POINTS
OF INPUTTED COLOR SYSTEM
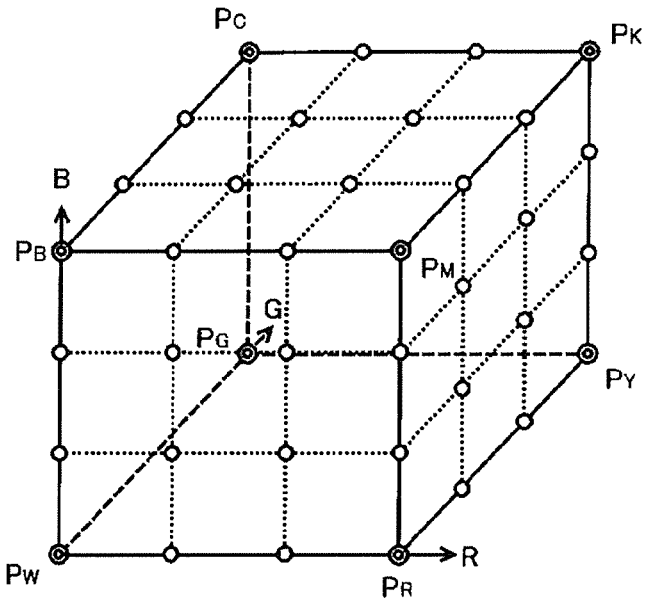
Fig. 12A
COLOR POINTS OF L*a*b* COLOR SYSTEM
(BEFORE SMOOTHING)
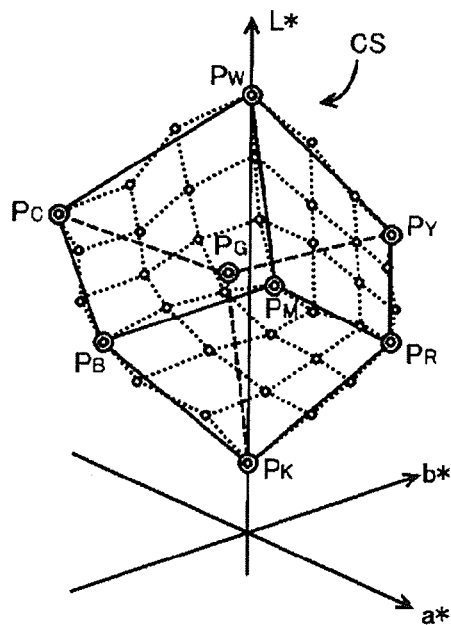
⇒ SMOOTHING
COLOR POINTS OF L*a*b* COLOR SYSTEM
(AFTER SMOOTHING)
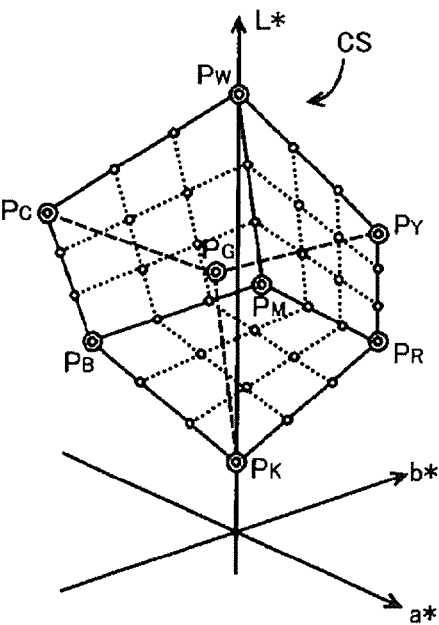
Fig. 12B
Fig. 12C

Fig. 14A
COLOR POINTS TARGETED
BY SMOOTHING PROCESS
(L*a*b* COLOR SPACE)

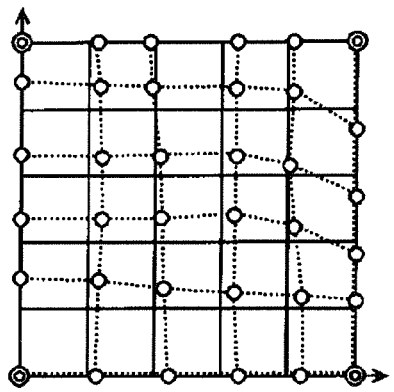

Fig. 14B
AFTER VERY SMALL MOVEMENTS
BY MECHANICAL MODEL
(L*a*b* COLOR SPACE)

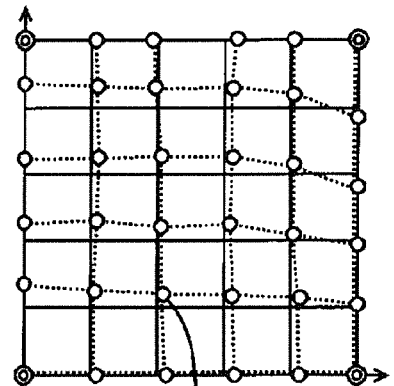

LABt

Fig. 14C
SEARCH FOR INK AMOUNTS (OPTIMIZATION PROCESS)

SEARCH FOR INK AMOUNTS FOR MINIMIZING OBJECTIVE FUNCTION E $$E = \left|\overrightarrow{LAB_t} - \overrightarrow{LAB_{FM}}(Ij)\right|^2 + \alpha \cdot GI(Ij) + \beta \cdot BI(Ij)$$

$\overrightarrow{LAB_t}$ : TARGET Lab VALUE $\overrightarrow{LAB_{FM}}(Ij)$ : Lab VALUE CONVERTED FROM INK AMOUNTS Ij BY FORWARD MODEL $GI(Ij)$ : GRAININESS INDEX $BI(Ij)$ : BRONZING INDEX VALUE

Fig. 14D
RECALCULATION OF Lab VALUE FROM INK AMOUNTS

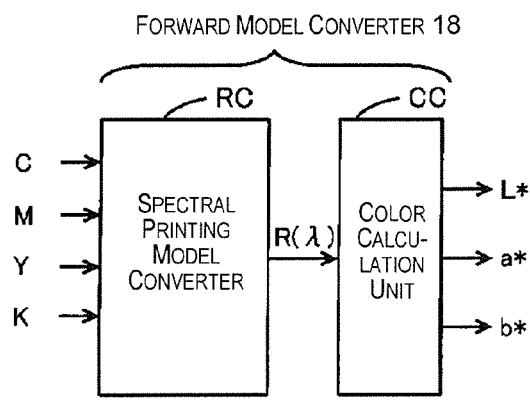

BRONZING INDEX VALUE CALCULATION METHOD, BRONZING INDEX VALUE CALCULATION DEVICE, AND PRINTING DEVICE

CROSS-REFERENCE TO RELATED APPLICATIONS

This application claims priority to Japanese Patent Application No. 2011-081714 filed on Apr. 1, 2011 and Japanese Patent Application No. 2011-132808 filed on Jun. 15, 2011. The entire disclosures of Japanese Patent Application Nos. 2011-081714 and 2011-132808 are hereby incorporated herein by reference.

BACKGROUND

1. Technical Field

The present invention relates to creating an index for evaluating bronzing.

2. Background Technology

Sheet paper and other media as well as ink and other recording agents for accentuating the gloss of a printed object are known in the art. These recording agents and media are used in specific applications (for example, when there is a desire to heighten the image clarity of a photographic print or the like) and are a contributing factor to highlighting the texture of a printed object (e.g., see Patent Citations 1 to 3).

One known phenomenon occurring due to the aforesaid gloss is bronzing (also called the bronzing phenomenon). Bronzing is a phenomenon where, when a printed object is observed in a state of specular reflection relative to a light source, the coloring is perceived as being different from the observation in a normal state of diffuse reflection, simulating the appearance of a metallic gloss. The occurrence of bronzing in a printed object is not preferable, because the coloring of the printed object is altered by the relative positional relationship between the printed object and an observer. Bronzing is generated by various different factors, such as the combination of inks and other recording agents or the combination of the recording agent with the media onto which the recording agent is recorded.

For this reason, in a disclosed technique (e.g., see Patent Citation 4), the bronzing properties of a printed object are calculated on the basis of the hue thereof (strictly speaking, the L*a*b* value), and the calculated value is used in selecting an optimal combination of inks.

Japanese Laid-open Patent Publication No. 2005-194500 (Patent Document 1), Japanese Laid-open Patent Publication No. 2005-274340 (Patent Document 2), Japanese Laid-open Patent Publication No. 2010-52247 (Patent Document 3) and Japanese Laid-open Patent Publication No. 2007-288270 (Patent Document 4) are examples of the related art.

SUMMARY

Although evaluations made been made where the coloring of a printed object has been measured as a value for evaluating the bronzing of the printed object, no disclosure has yet been made in regard to calculating an index value for quantitatively representing the degree of bronzing of the printed object.

The invention is contrived in view of the aforesaid problem, it being an advantage thereof to provide a calculation method and calculation device for a bronzing index value as well as a printing device in accordance with the degree of bronzing, the bronzing index value being an index value for quantitatively representing the degree of bronzing for a printed object.

To resolve the aforesaid problem, an aspect of the invention is configured to include: calculating a difference between a hue angle of a colorimetric value of a printed object with respect to diffuse reflection and a hue angle of a colorimetric value of a printed object with respect to specular reflection; calculating a difference between a standard chroma with respect to an observational light source and a chroma of a colorimetric value of the printed object with respect to specular reflection under the observational light source; and calculating a bronzing index value on the basis of a value obtained by multiplying the calculated difference of the hue angles by the calculated difference of the chromas. In such a case, because the degree of bronzing in a printed object under predetermined printing conditions is calculated as an index value, the evaluation of the degree of bronzing generated in the printed object and the like can be handled quantitatively.

In calculating the index value, a weighting can be set such that the bronzing index value is lower at a lower chroma. In such a case, a lower chroma can correspondingly take a lower bronzing index value even when the multiplied difference of the hue angle is a smaller value than the difference of the chromas.

In calculating the index value, the difference of the hue angles and the difference of the chromas can be normalized. In such a case, a lower chroma can correspondingly take a lower bronzing index value even when the multiplied difference of the hue angle is a smaller value than the difference of the chromas.

The bronzing index value can also be acquired for individual printed objects. In such a case, the evaluation and the like of the bronzing generated for the printed objects can be handled quantitatively for each category of sheet paper even though the degree of bronzing generated varies depending on the category of sheet paper.

To resolve the aforesaid problem, another aspect of the invention can also be a bronzing index value calculation device including: difference calculating means for calculating a difference between a hue angle of a colorimetric value of the printed object with respect to diffuse reflection and a hue angle of a colorimetric value of the printed object with respect to specular reflection; chroma difference calculating means for calculating the difference between a standard chroma with respect to an observational light source and a chroma of a colorimetric value of the printed object with respect to specular reflection under the observational light source; and index value calculating means for calculating a bronzing index value on the basis of a value obtained by multiplying the calculated difference of the hue angles by the calculated difference of the chromas. In such a case, because the degree of bronzing in a printed object under predetermined printing conditions is calculated as an index value, the evaluation and the like of the degree of bronzing generated in the printed object can be handled quantitatively.

Further, to resolve the aforesaid problem, another aspect of the invention can be a printing device for discharging ink according to a first discharge amount onto a first printed object in a case where a first gradation value has been inputted and for discharging ink according to a second discharge amount different from the first discharge amount onto a second printed object different from the first printed object in a case where the first gradation value has been inputted, the printing device having, among all the relationships between the gradation value and the discharge amount, at least one relationship between the gradation value and the discharge amount such that the difference between the degree of bronzing in the case where the ink is discharged onto the first printed object according to the first discharge amount and the degree of bronzing in the case where the ink is discharged onto the second printed object according to the second discharge amount is less than the difference between the degree of bronzing in the case where the ink is discharged onto the first printed object according to the first discharge amount and the degree of bronzing in the case where the ink is discharged onto the second printed object according to the first discharge amount. In such a case, discharging according to a discharge amount in accordance with the category of sheet paper makes it possible to print with a relative reduction in the degree of bronzing generated by a degree which varies depending on the category of sheet paper, even though the degree of bronzing generated varies depending on the category of sheet paper.

Further, the printing device can also have at least one relationship between the gradation value and the discharge amount such that the difference between A and B is less than the difference between A and C, where A is the bronzing index value in the case where ink is discharged onto the first printed object according to the first discharge amount; B is the bronzing index value in the case where ink is discharged onto the second printed object according to the second discharge amount; and C is the bronzing index value in the case where ink is discharged onto the second printed object according to the first discharge amount. In such a case, the evaluation and the like of the degree of bronzing generated for the printed object can be handled quantitatively.

Further, in the printing device, the bronzing index value can be calculated by a bronzing index value calculation method including: calculating a difference between a hue angle of a colorimetric value of a printed object with respect to diffuse reflection and a hue angle of a colorimetric value of a printed object with respect to specular reflection; calculating the difference between a standard chroma with respect to an observational light source and a chroma of a colorimetric value of the printed object with respect to specular reflection under the observational light source; and calculating a bronzing index value on the basis of a value obtained by multiplying the calculated difference of the hue angles by the calculated difference of the chroman. In such a case, the evaluation and the like of the degree of bronzing generated for the printed object can be handled quantitatively.

This specification is a disclosure of the specific configuration and effects according to the invention.

BRIEF DESCRIPTION OF THE DRAWINGS

Referring now to the attached drawings which form a part of this original disclosure:

FIG. 8 is a drawing for describing an index value table T;

FIG. 12 is a drawing illustrating the correspondence relationship between an input grid point and the coordinate values of an L*a*b* color space in a smoothing process;

FIG. 14 is a descriptive drawing illustrating the process content of steps S820 to S850 in FIG. 13.

DETAILED DESCRIPTION OF EXEMPLARY EMBODIMENTS

The following is a description of embodiments of the invention, in accordance with the sequence below:
1. A bronzing index value calculation method 1;
2. A bronzing index value calculation method 2; and
3. An LUT creation method.
4. Other Embodiments 1. Bronzing Index Value Calculation Method 1

Figure 1:
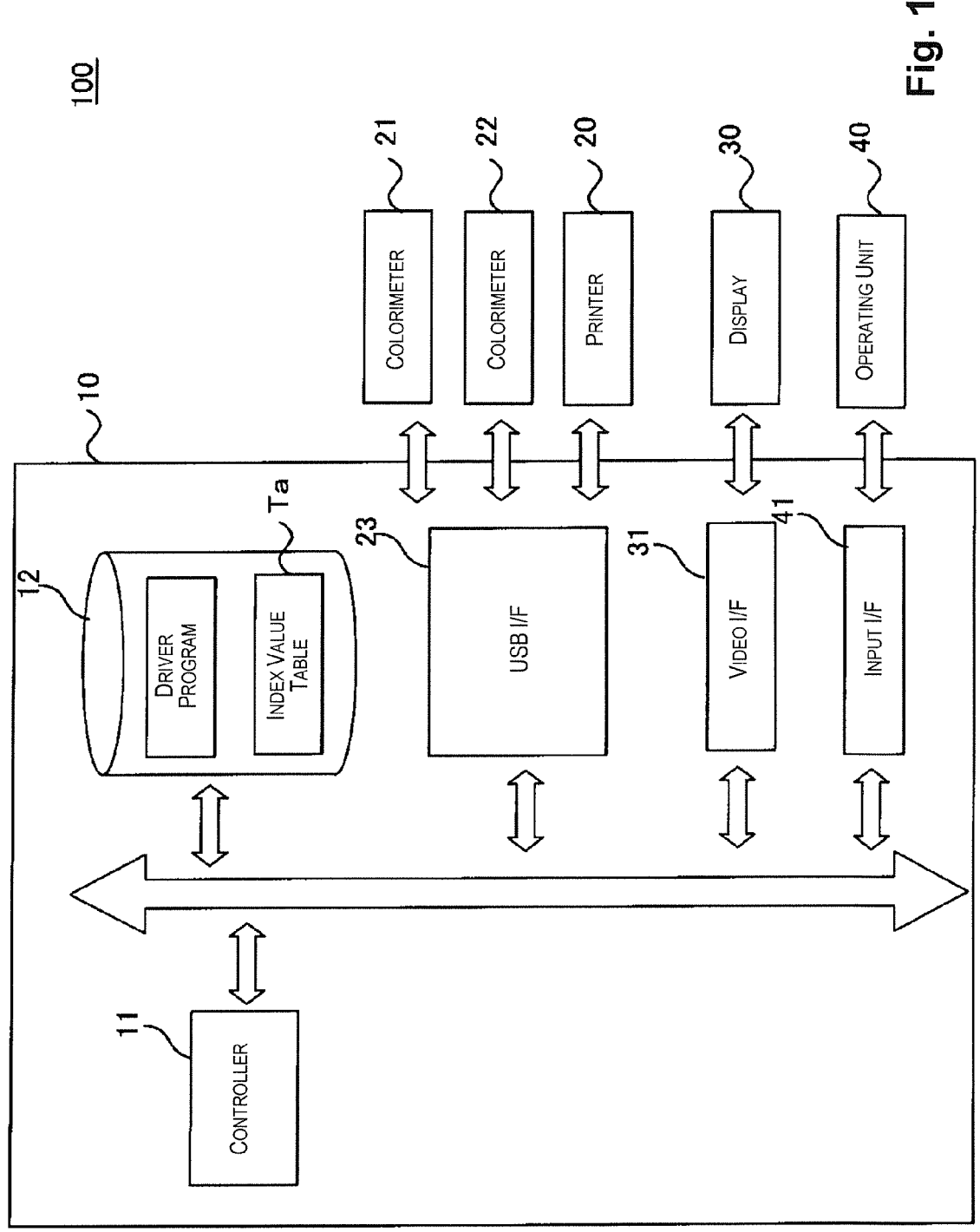
FIG. 1 is a configurational block diagram for illustrating the configuration of an index value acquisition system 100.

The following is a description of an embodiment embodying a bronzing index value calculation method according to the invention. FIG. 1 is a configurational block diagram for describing the configuration of an index value acquisition system 100.

The index value acquisition system 100 is configured to comprise a computer 10, a printer 20, and colorimeters 21, 22. The index value acquisition system 100 drives the colorimeters 21, 22 and the printer 20 on the basis of the integrated control of the computer 10, and calculates bronzing indices (also recited as a bronzing index value BI and a bronzing index value BI(Ij) relative to an ink amount Ij used by a printer (not limited to being the printer 20).

The computer 10 is provided with a controller 11, a memory unit 12, a USB interface (I/F) 23, a video I/F 31, an input I/F 41, and other components. The controller 11 provided to the computer 10 reads a program stored in the memory unit 12 and executes a calculation along the program, whereby a predetermined process is executed. The computer 10 also functions as a bronzing index value calculation device for performing a process for calculating an index value at the ink amount Ij.

The memory unit 12 is, for example, a hard disk drive (HDD), in which is stored an index value table Ta in which index values involved in bronzing are recorded. The memory unit 12 records various types of driver programs for causing the controller 11 to control the drive of the printer 20 or for causing the colorimeter 21 to acquire a colorimetric value.

The computer 10 executes a calculation in accordance with a program and controls the printer 20 via the USB I/F 23 or the like, and thereby also functions as a printing control device. Specifically, the computer 10 acquires image data which is to be printed, color-converts the image data by pixel units using a color conversion profile, and performs a halftone process or microwave process on the color-converted image data, thus generating printing data. The printing data is outputted to the printer 20 via the USB I/F 23. The printer 20 thereby executes printing based on the printing data. The computer 10 is also connected to a display 30 via the video I/F 31, and is connected to a keyboard, mouse, or other operating unit 40 via the input I/F 41.

The colorimeter 21 takes colorimetric measurements of a colorimetry subject and supplies a colorimetric value to the computer 10. The colorimeter 21 includes: a light source constituted of a xenon lamp or the like (for example, a standard D50 light source); a colorimetry unit for measuring the reflection intensity of the light reflected off the colorimetry subject (also recited as the spectral reflectivity), and a colorimetric value calculation unit for calculating a colorimetric value (which in the present embodiment is an L*a*b* value) using the spectral reflectivity acquired by the colorimetry unit. Herein, the colorimetry unit of the colorimeter 21 is configured so as to receive light reflected diffusely by the colorimetry subject (also recited as diffuse reflection light) and to acquire the reflection intensity thereof.

The colorimeter 22, similarly with respect to the colorimeter 21, is configured to include a light source, a colorimetry unit, and a colorimetric value calculation unit; and supplies a colorimetric value to the computer 10. In the present embodiment, the colorimetry unit of the colorimeter 22 is configured so as to receive light providing a specular reflection of the colorimetry subject (also recited as specular reflection light) and to acquire the reflection intensity thereof.

The printer 20 sprays a medium (sheet paper) with ink and forms an image on the basis of the control from the computer 10. The present embodiment assumes a color printer capable of using four varieties of ink; i.e., cyan (C), magenta (M), yellow (Y), and black (K). As shall be apparent, the variety of ink used by the printer 20 is not limited to four varieties; light cyan (Lc), light magenta (Lm), and light black (Lk) can also be added thereto.

Figure 2:
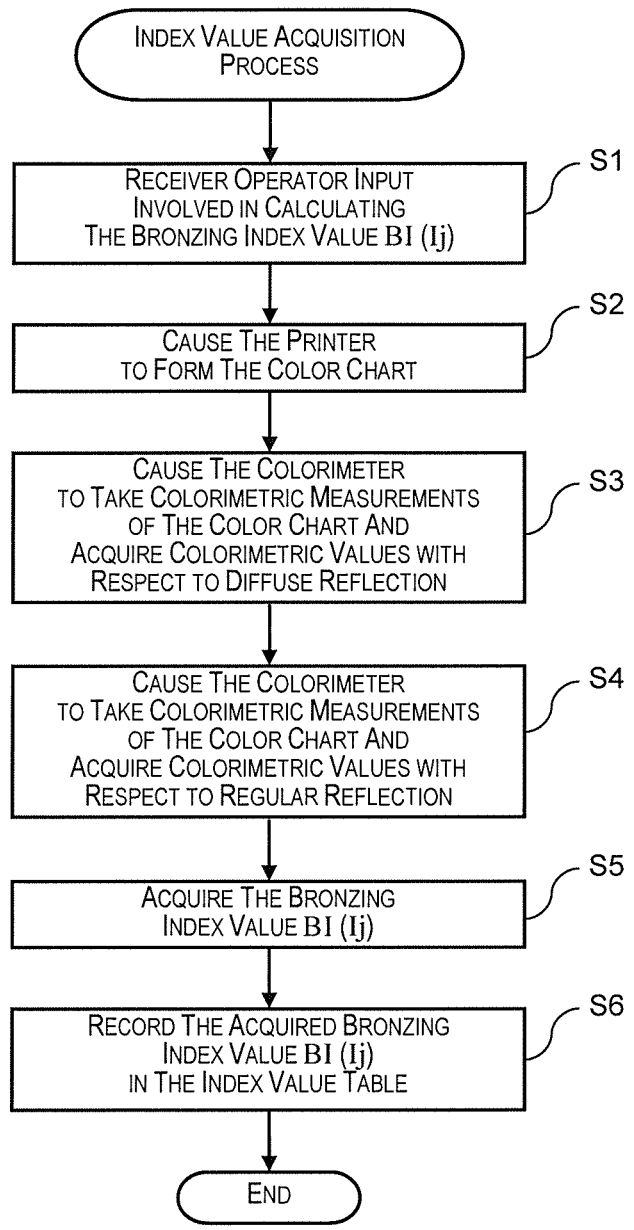
FIG. 2 is a flow chart for illustrating a process executed by the index value acquisition system 100.

FIG. 2 is a flow chart for illustrating a process executed by the index value acquisition system 100. The computer 10 creates the bronzing index value BI for each ink amount Ij, according to the process illustrated in FIG. 2. The degree of bronzing for a certain ink amount Ij is indexed according to the bronzing index value BI calculated according to this process. Specifically, a higher bronzing index value BI for an ink amount Ij indicates a less desirable degree of bronzing, and a lower bronzing index value for an ink amount Ij indicates a more desirable degree of bronzing. The bronzing index value is defined herein such that a higher value corresponds to a less favorable degree [of bronzing].

A user operates the operating unit 40 of the computer 10 to perform an input on a UI screen (not shown), whereupon the computer 10 receives the input in step S1. The category of sheet paper for which a bronzing index value BI is to be created is selected by the aforesaid input. For example, examples of sheet paper which can be selected on the UI screen include "plain paper," "cardboard (matte paper)," "coated paper (glossy paper)," and "special paper." The reason for selecting the sheet paper for which the bronzing index value BI is to be created is that the resulting degree of bronzing varies depending on the category of sheet paper.

Figure 3:
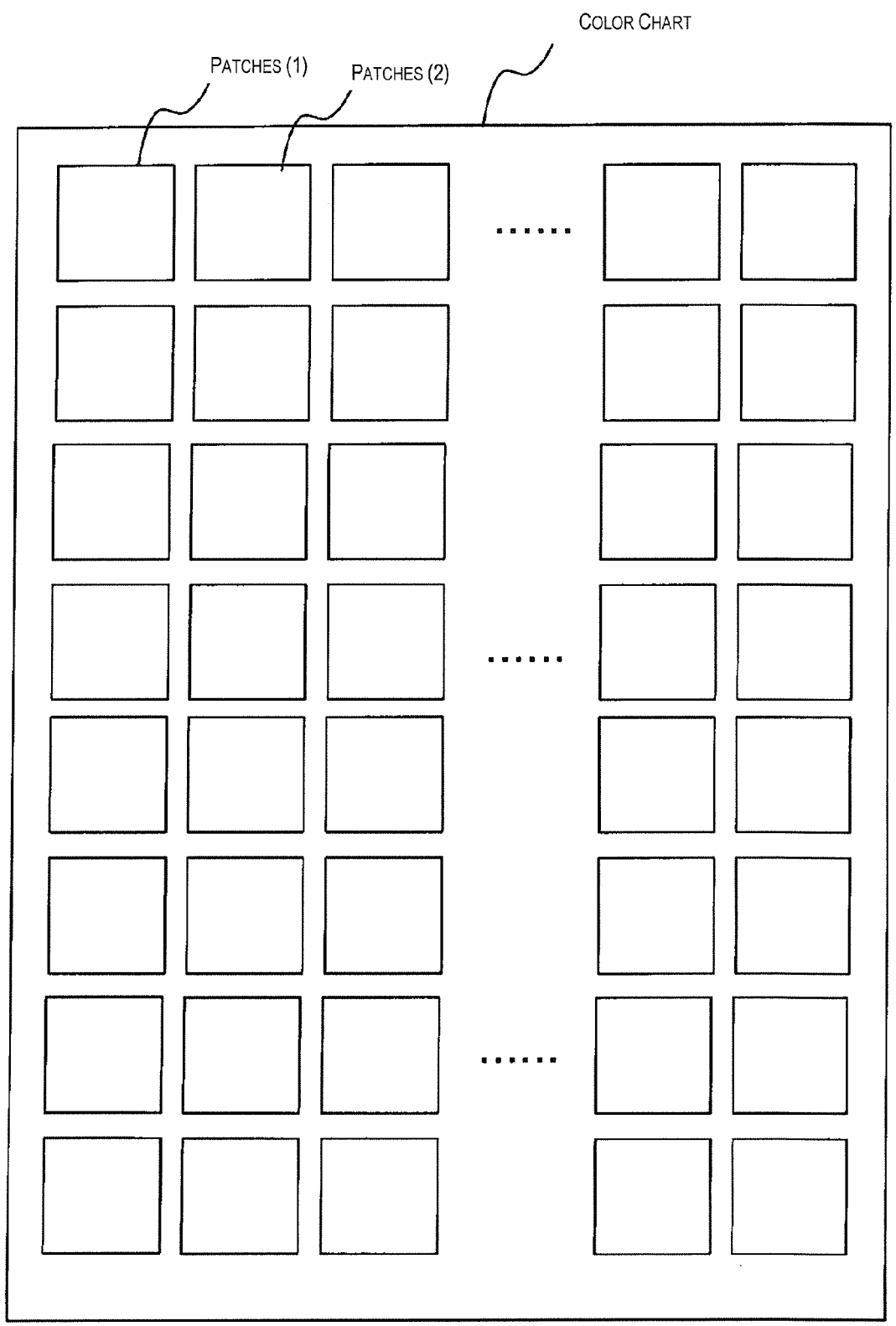
FIG. 3 is a drawing for illustrating a color chart formed by a printer 20.

In step S2, the computer 10 causes the printer 20 to form a color chart. FIG. 3 is a drawing for illustrating a color chart formed by the printer 20. The color chart according to the present embodiment is constituted of a horizontal and vertical array of a plurality of patches (i). In each of the patches (i), each of the primary-color inks (C, M, Y, K) to be sprayed by the printer 20 is changed by the ink amount Ij, so that a predetermined gradation value is formed. The gradation value of the primary-color inks for forming the patches (i) is set in accordance with the gradation value used by the printer equipped with the ink. The ink amount Ij is, in the present embodiment, constituted of a primary-color ink, but can also be a combination of primary-color inks. The phrase "color chart" in the present specification is used in a broad range of meanings which is not limited to patches of chromatic color but also includes patches of achromatic color.

Figure 4A:
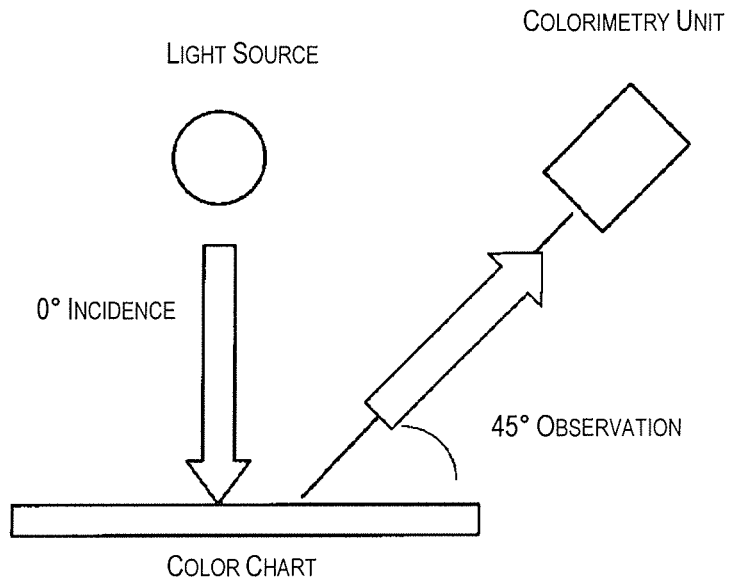
FIG. 4 is a drawing for illustrating a method by which the colorimeter performs colorimetric measurements of the color chart.
Figure 4B:
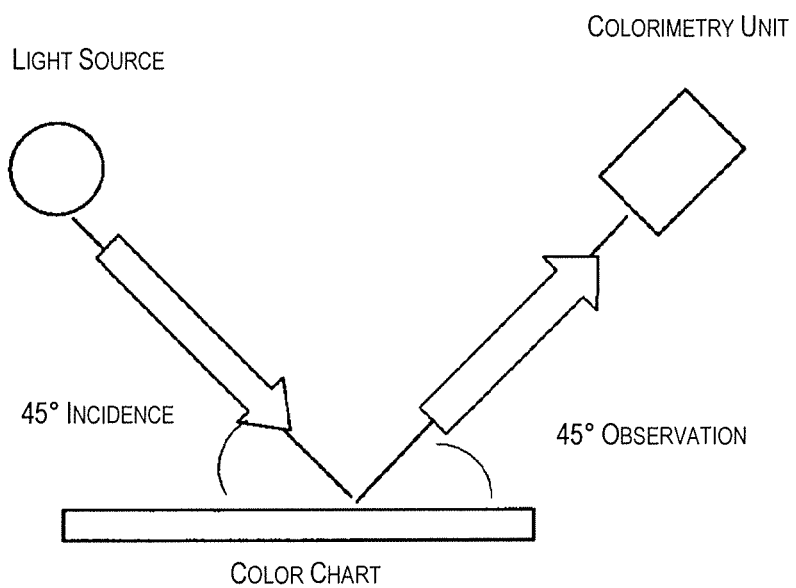

In step S3, the computer 10 causes the colorimeter 21 to take colorimetric measurements of the color chart and acquires the colorimetric value of each of the patches (i). FIG. 4 is a drawing for illustrating a method by which the colorimeter makes colorimetric measurements of the color in the color chart. FIG. 4A illustrates a colorimetry method used by the colorimeter 21. FIG. 4B illustrates a colorimetry method used by the colorimeter 22.

As illustrated in FIG. 4A, in the colorimeter 21, the light source is arranged to be orthogonal (at 0°) to the color chart, the colorimetry unit is arranged to be at a 45° angle relative to the color chart, and colorimetric measurements are taken of each of the patches (i). For this reason, a colorimetric value at diffuse reflection is acquired by the colorimeter 21 for each of the patches (i). The colorimeter 21 acquires a colorimetric value for all of the patches (i) for forming the color chart.

In step S4, the computer 10 causes the colorimeter 22 to take colorimetric measurements of the color chart and acquires the colorimetric value of each of the patches (i). As illustrated in FIG. 4B, in the colorimeter 22, the light source is positioned at a 45° angle to the color chart, the colorimetry unit is positioned at a −45° angle relative to the color chart, and colorimetric measurements are taken of each of the patches (i). For this reason, a colorimetric value at specular reflection is acquired by the colorimeter 21 for each of the patches (i).

In step S5, the computer 10 acquires a bronzing index value BI from each of the colorimetric values acquired in steps S3 and S4. The following two points are included as phenomena which are generally recognized as being bronzing:

(Phenomenon 1): The color observed at an angle that represents specular reflection relative to the observational light source and the color observed under diffusion reflection have different colorings (hues).

(Phenomenon 2): The color observed at an angle that represents specular reflection relative to the observational light source and the color of the observational light source have different colorings (hues).

For this reason, in the present embodiment, phenomenon 1 and phenomenon 2 are quantified and the bronzing index value BI is calculated.

Figure 5:
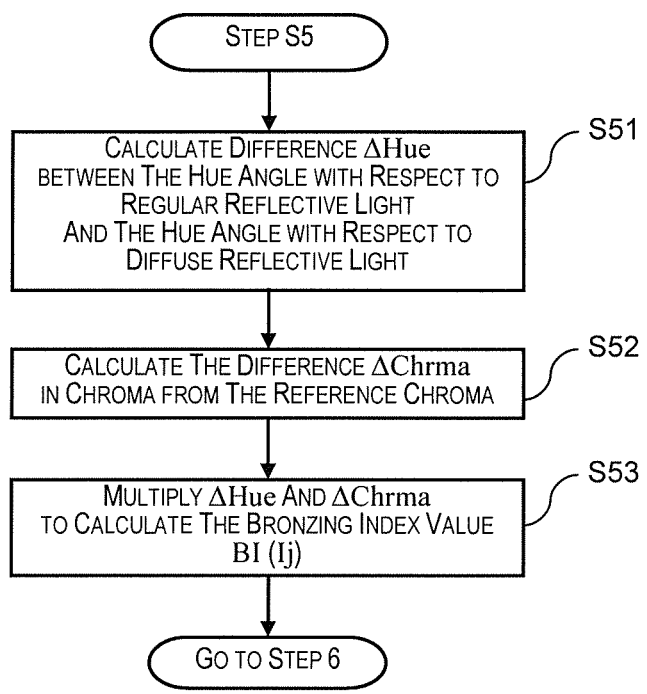
FIG. 5 is a flow chart for providing a detailed illustration of the process in a step S5.

FIG. 5 is a flow chart for providing a detailed illustration of the processing in step S5. FIG. 6 is a drawing for describing a bronzing index value.

Figure 6A:
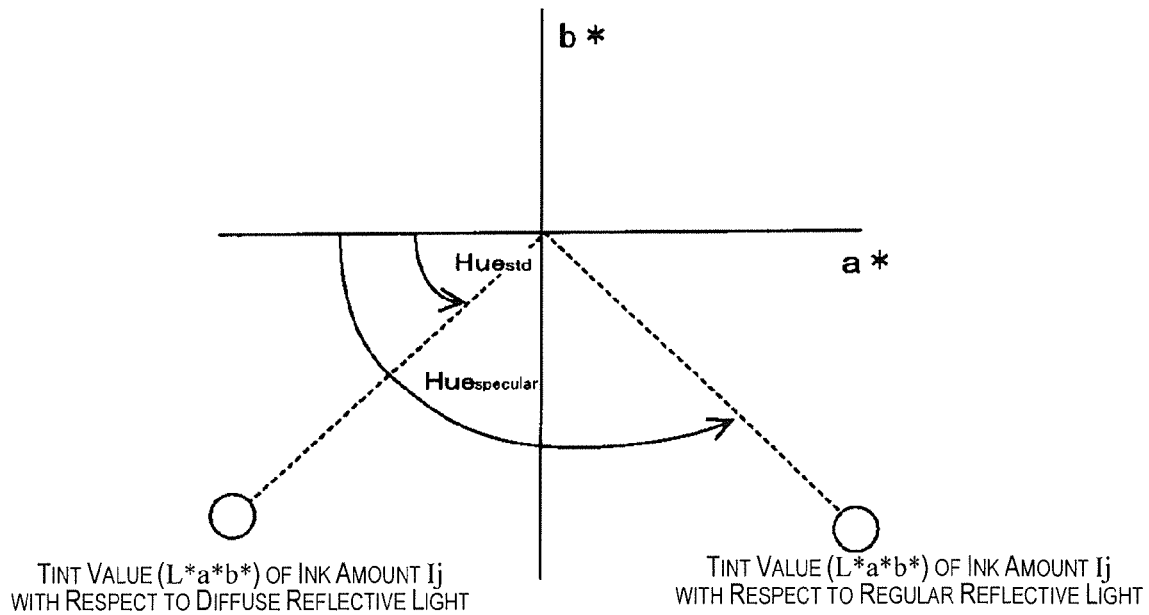
FIG. 6 is a drawing for describing a bronzing index value.

In step S51 of FIG. 5, the computer 10 calculates ΔHue, which is the difference between a hue angle $Hue_{std}$ with respect to diffuse reflection and a hue angle $Hue_{specular}$ with respect to specular reflection. Specifically, in this step, the disparity in coloring under normal observation (diffuse reflection) from the coloring observed in specular reflection, represented by phenomenon 1, is determined as the difference of the hue angles Hue. In FIG. 6A, the hue angles are calculated as angles on a hue circle. In a case where the coloring with respect to specular reflection and the coloring with respect to diffuse reflection are different, the hue angles Hue on the hue circle are also different, and therefore a greater difference between the two colorings corresponds to a greater angle of difference as well. For this reason, in this step, phenomenon 1 is quantified as the difference in hue angles Hue.

For this reason, the computer 10 calculates the hue angle $Hue_{std}$ from the colorimetric values (L*a*b* values) of the patches (i) with respect to diffuse reflection as acquired in step S3. The computer 10 also calculates the hue angle $Hue_{specular}$ from the colorimetric values (L*a*b* value) of the patches (i) with respect to specular reflection acquired in step S4. In general, the hue angles Hue can be determined by the following Formula (1).

[Formula 1]

$$Hue = atan\left(\frac{a^*}{b^*}\right) \quad (1)$$

a* and b* are the a* and b* values of the colorimetric value (the L*a*b* value).

The following Formula (2) is used to calculate a difference ΔHue in hue angles for each of the patches (i) (ink gradation value) on the basis of each hue angles $Hue_{std}$, $Hue_{specular}$ thus determined.

[Formula 2]

$$\Delta Hue(Ij) = Hue_{std}(Ij) - Hue_{specular}(Ij) \quad (2)$$

The range of values that can be taken by ΔHue is 0≤ΔHue≤2π (in radians). The difference calculation step and the difference calculating means of the invention are achieved by the process of step 51.

Figure 6B:
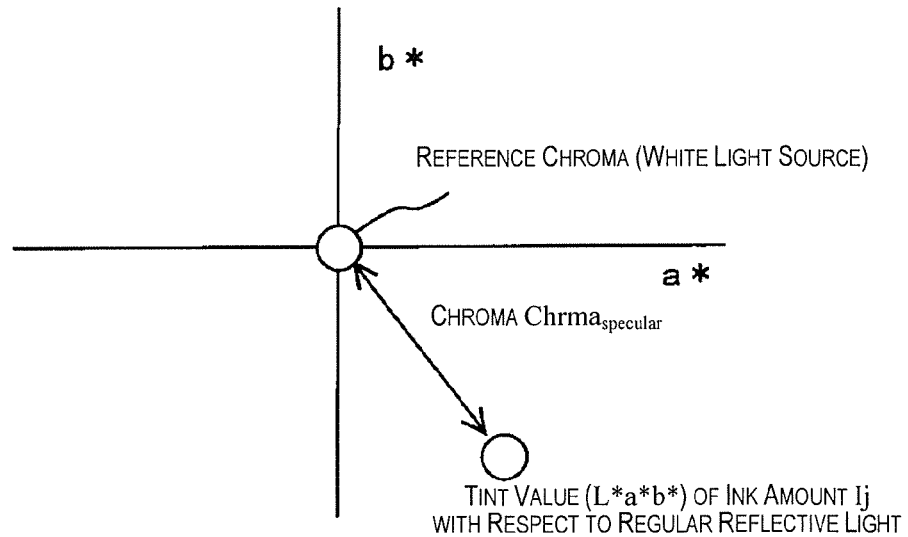

In step S52, the computer 10 calculates a difference ΔChroma from a reference chroma with specular reflection. That is, in this step, the phenomenon where the coloring is perceived as being different with specular reflection relative to the coloring of the observational light source, represented by phenomenon 2, is quantified as the difference ΔChroma of the chroma with specular reflection. As illustrated in FIG. 6B, in a case where the coloring with specular reflection is different with the same observational light source, a chroma $Chroma_{specular}$ in which an object is viewed with specular reflection is different relative to the chroma under the observational light source (also recited as the reference chroma) on the hue circle. Herein, the chroma Chroma can generally be calculated by the following Formula (3).

[Formula 3]

$$Chroma = \sqrt{a^{*2} + b^{*2}} \quad (3)$$

In the present embodiment, white light is used as the observational light sources in the colorimeter 21 and the colorimeter 22, wherefore the reference chroma is the smallest possible value (≈0). For this reason, the chroma with specular reflection can be used as the chroma difference ΔChroma. The chroma difference calculation step and the chroma difference calculating means of the invention are achieved by the aforesaid process of step S52.

In step S53, the computer 10 multiples each of the values (ΔHue, ΔChroma) in which phenomenon 1 and phenomenon 2 have been quantified and calculates a bronzing index value BI (Ij). That is, the bronzing index value BI (Ij) can be calculated by the following Formula (4).

[Formula 4]

$$BI(Ij) = \Delta Hue(Ij) \times \Delta Chroma(Ij) \times weight(Ij) \quad (4)$$

Herein, "weight" is an adjustment weighting such that the bronzing index value BI (Ij) becomes lower at a lower chroma. In the present embodiment, the weighting weight is calculated as a sigmoid function as illustrated by the following Formula (5).

[Formula 5]

$$Weight = \frac{1}{1 + e^{-10A}} \quad (5)$$

$$A = \frac{Chroma_{specular}}{Chroma_{max}} - 0.5$$

Figure 7:
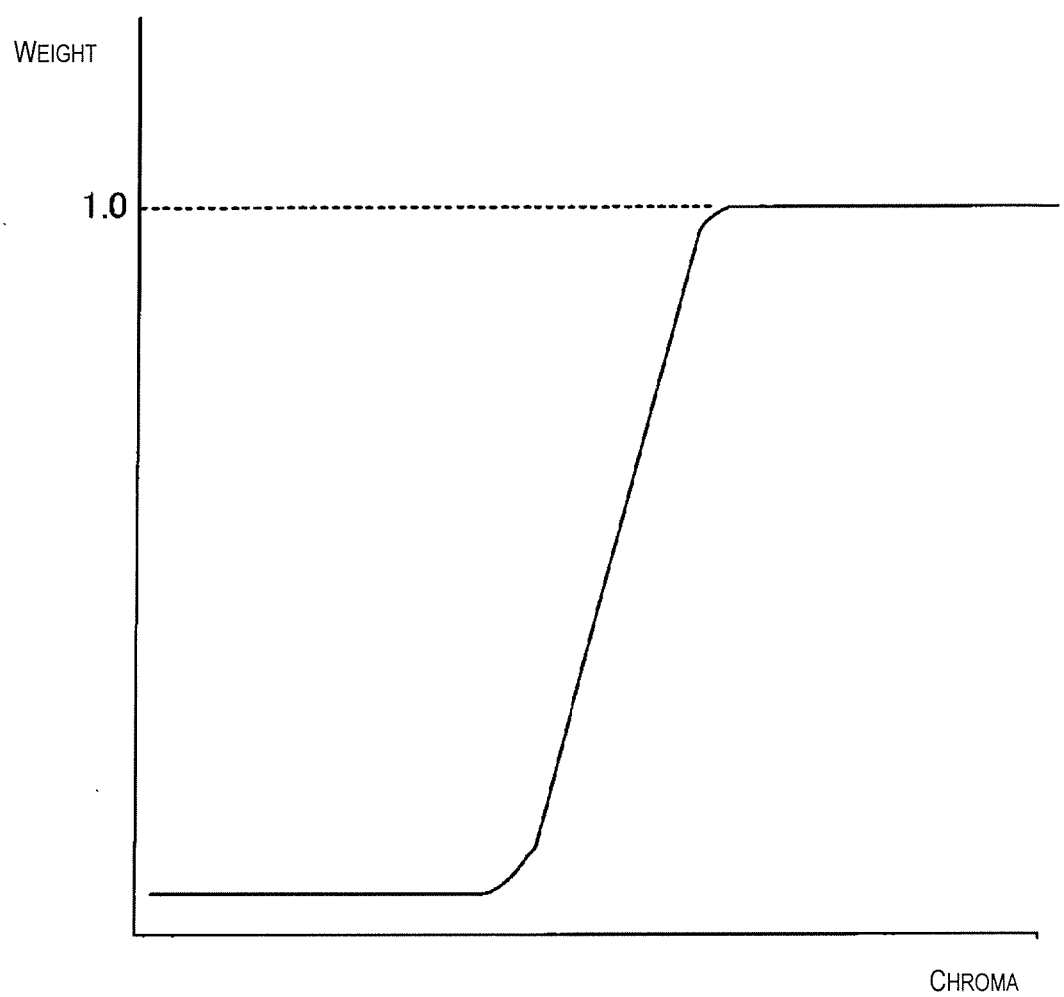
FIG. 7 is a drawing illustrating a weighting weight according to the present embodiment.

$Chroma_{specular}$: Chroma with specular reflection
$Chroma_{max}$: Threshold chroma value for determining a low chroma FIG. 7 is a drawing illustrating the weighting weight according to the present embodiment. The weighting weight, by virtue of being a sigmoid function, increases monotonically in accordance with the chroma with diffuse reflection ($Chroma_{specular}$) and has a single inflection point. That is, the weighting weight is as small as possible in the small chroma region, and the weighting weight increases bounded by a certain chroma ($Chroma_{max}$). After a certain amount of time, the weighting weight becomes saturated in the vicinity of "1." For this reason, the weighting weight is added as a part of the bronzing index value BI (Ij), whereby, in the low chroma region, the value of the bronzing index value BI (Ij) decreases (i.e., becomes a more desirable value as an index value) and, in the high chroma region, the value of the bronzing index value BI (Ij) increases (i.e., becomes a less desirable value as an index value).

A reason for which the bronzing index value BI (Ij) is weighted by a sigmoid function in accordance with the chroma is that the difference ΔHue of the hue angles and the chroma difference ΔChroma have different ranges of values they can take, and therefore the degrees of influence must be equalized. That is, the difference ΔHue of the hue angles is a value in the range of 0≤ΔHue≤2π (units: radians), whereas the chroma difference ΔChroma is a value in the range of 0≤Chroma≤50. For this reason, a difference ΔHue of the hue angles having a smaller value becomes dominant when the two (ΔHue and ΔChroma) are simply multiplied together. It is also necessary for the bronzing index value BI (Ij) to be set such that a lower chroma corresponds to a more favorable value therefor (corresponds to a lower index value). That is, the value must be adjusted such that in the calculation of ΔChroma, a smaller chroma $Chroma_{specular}$ with specular reflection corresponds to a decreased likelihood of the generation of bronzing. For this reason, the weighting weight is added such that the bronzing index value BI (Ij) takes a lower value for a lower chroma. The index value calculation step and the index value calculating means of the invention are achieved by the aforesaid process of step S53.

Returning now to FIG. 2, in step S6, the computer 10 records the index value acquired in step S5 in the index value table Ta. FIG. 8 is a drawing for describing the index value table Ta. As illustrated in FIG. 8, the index value table Ta has a bronzing index value BI (Ij) set for each of the sheet papers used by the printer (which, in the present embodiment, are "plain paper," "cardboard," "coated paper," and "special paper"). That is, the ink value Ij (the gradation value) and the bronzing index value BI (Ij) corresponding to the ink amount Ij are recorded for each of the sheet papers. For this reason, in the creation of the LUTs in the printer 20 (described below), the index value table Ta is referenced and the optimum ink amount Ij is sought. As shall be apparent, the index value recorded in the index value table Ta is not limited to the formats of each of the sheet papers; printing control information in the computer 10 (for example, information on the weight of the ink droplets sprayed during printing) and the like can also be added.

2. Bronzing Index Value Calculation Method 2

In the course of calculating the bronzing index value BI, the difference ΔHue of the hue angles and the chroma difference ΔChroma can each also be normalized. As described above, the hue angle difference ΔHue has a smaller value than the chroma difference ΔChroma, and therefore the hue angle difference ΔHue becomes dominant in a bronzing index value BI involving simple multiplication. For this reason, the hue angle difference ΔHue and the chroma difference ΔChroma can each be normalized to a value 0 to 1, the bronzing index value BI (Ij) then being calculated by the values after normalization.

That is, in step S53 of FIG. 5, the computer 10 uses the difference ΔHue of the hue angles and the difference ΔChroma of the chroman after normalization to calculate the bronzing index value BI (Ij). In step S6 of FIG. 2, the computer 10 records the calculated bronzing index value BI (Ij) in the index value table Ta.

As has been described above, the present bronzing index value calculation method makes it possible to quantitatively handle the evaluation of the degree of bronzing generated during printing and the like because the degree of bronzing in the printed object under predetermined printing conditions is calculated as an index value.

3. LUT Creation Method

Figure 9:
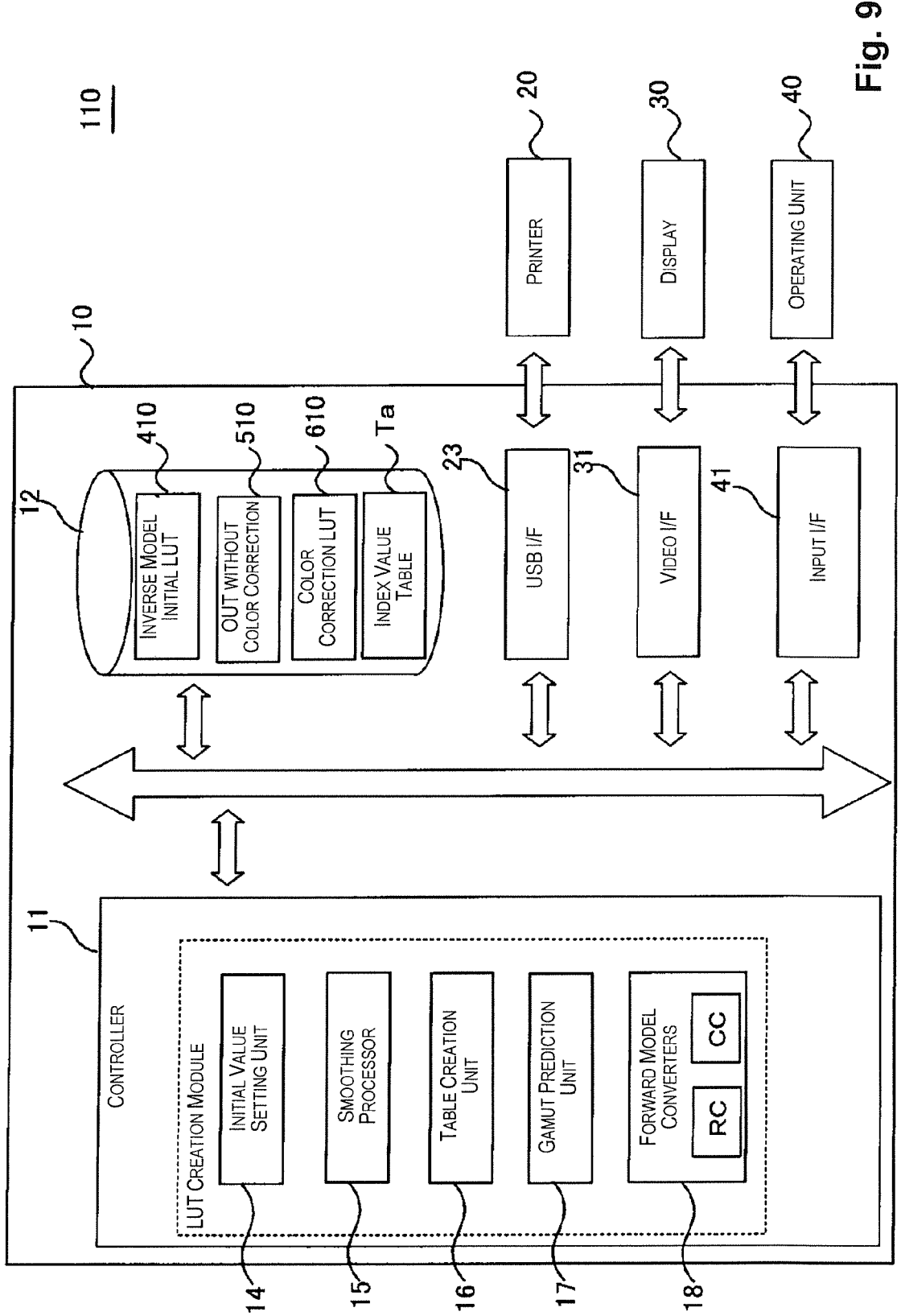
FIG. 9 is a configurational block diagram for illustrating an LUT creation system 110.

The following is a description of the LUT creation method, using the bronzing index value BI created by the present index value creation method. FIG. 9 is a configurational block diagram illustrating an LUT creation system 110. The present LUT creation system 110 is configured from the computer 10, the printer 20, and a colorimeter (not shown).

The memory unit 12 of the computer 10 according to the LUT creation method records a program or color conversion profile (for example, an inverse model initial LUT 410, an LUT 510 without color correction, and a color correction LUT 610, all to be described below), the index value table Ta in which index values involved in bronzing are recorded, and the like. "LUT" is an abbreviation for a look-up table.

The LUT 510 without color correction is a color conversion table for converting the gradation value of a predetermined inputted color space (for example, the RGB color space) to a combination of a plurality of different varieties of inks used by the printer 20 (the ink amount Ij). The RGB color space, which is the inputted color space of the LUT 510 without color correction, is not a so-called device-dependent color space, but rather is a virtual color space (alternatively, an abstract color space) that has been set without relation to any specific device. The LUT 510 without color correction is used when, for example, the color correction LUT 610 is created. The color correction LUT 610 is a look-up table for converting a standard device-dependent color space (for example, an sRGB color or the JAPAN COLOR 2001 color space) to the ink amount Ij of a specific printer. A description of the inverse model initial LUT 410 shall be described below.

An LUT creation module of the computer 10 has an initial value setting unit 14, a smoothing processor 15, a table creation unit 16, a gamut prediction unit 17, and a forward model converter 18. A description of the functions of each of these parts shall be provided below.

<<Creation of the Profile>>

Figure 10:
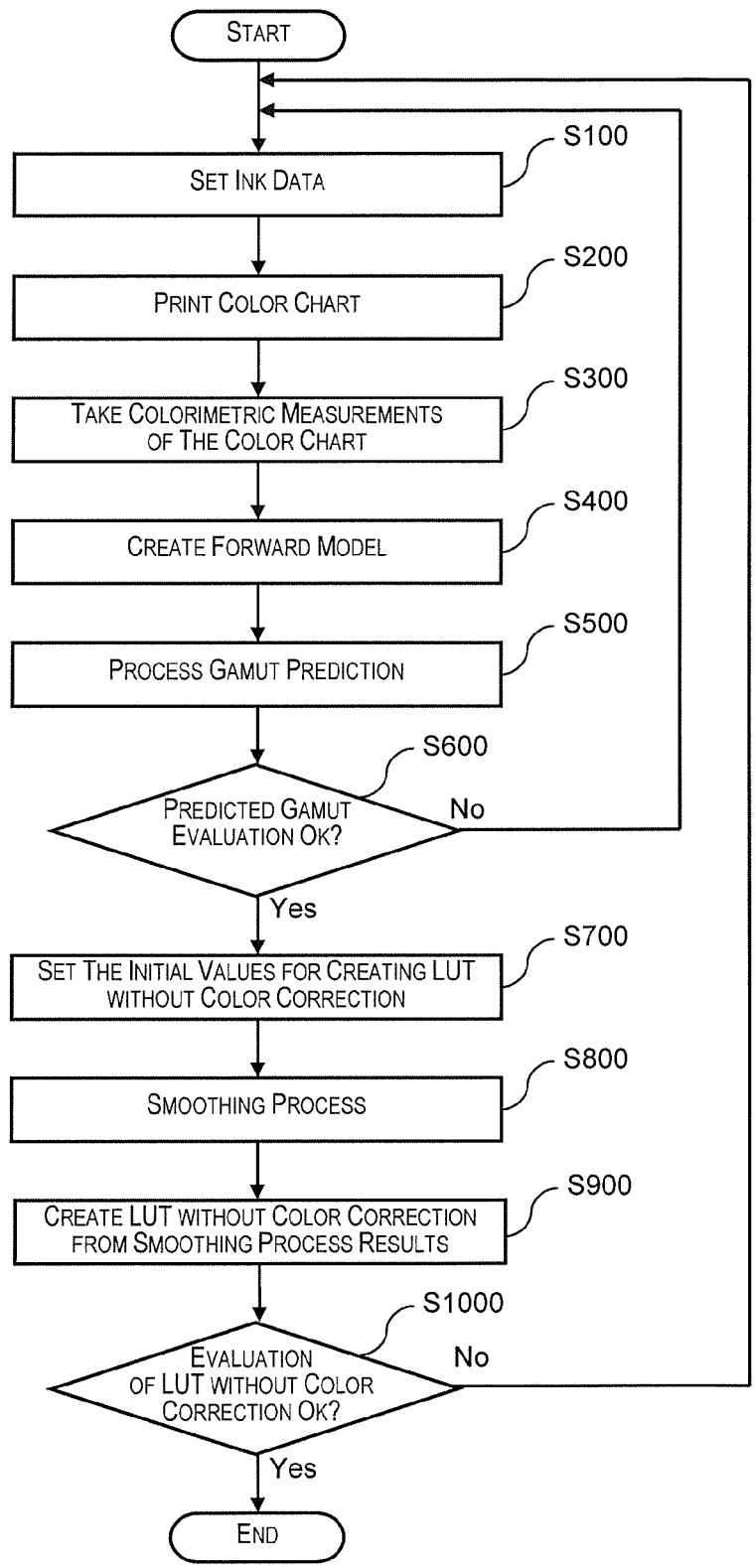
FIG. 10 is a flow diagram illustrating the entire process sequence during LUT creation without color correction.

FIG. 10 is a flow diagram illustrating the entire process sequence during LUT creation without color correction. In step S100, ink data is set. Herein, ink data refers to color, type, and duty limiting values and other values for the inks used by the printer 20.

A duty limiting value refers to the ink amount Ij that can be driven in a unit area of a medium (sheet paper). The duty limiting value is dependent on the type of medium and on the resolution of the image formed. For this reason, the duty limiting value is determined for each type of medium and for each printing resolution. In the present embodiment, printing is performed at a resolution of 1440×1440 dpi for photographic paper. The duty limiting value is a duty limiting value according to an ink monochrome or a duty limiting value according to the total of a plurality of colors (a total duty limiting value). For example, a duty limiting value at a certain resolution of a certain paper is determined so as to be 80% with monochrome and 120% with the total of respective colors.

In step S200, the color chart is printed. The printed flow chart is similar to the illustration in FIG. 3 and is constituted of the arrayed plurality of patches (i). Each of the patches (i) is formed with the predetermined ink amount Ij. The color chart is printed according to the simple combination of ink amounts Ij, without the use of the duty limiting value or color conversion table.

In step S300, for example, the colorimeter or a scanner (not shown) is used to take colorimetric measurements of each of the patches constituting the color chart. The colorimetry results are taken up by the computer 10, and a virtual sample in which associations have been made between the ink amounts Ij and the colorimetric values (L*a*b* values) is formed in the computer 10.

In step S400, a forward model (hereinafter also referred to as an FM) is created on the basis of the colorimetric results from the color chart (the virtual sample). A "forward model" signifies a conversion model for converting the ink amounts Ij to tint values (colorimetric values) of a device-independent color space. Conversely, an "inverse model" signifies a conversion model for converting tint values of a device-independent color space into ink amounts Ij. In the present embodiment, a CIE-L*a*b* color space is used as the device-independent color space. Hereinafter, a tint value of the CIE-L*a*b* color space is also simply called an "L*a*b* value" or "Lab value."

Figure 11:
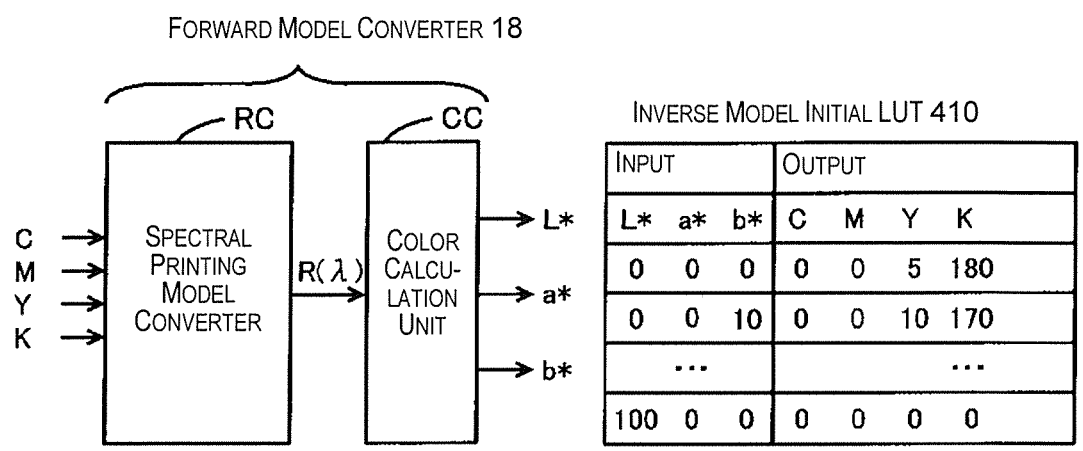
FIG. 11 is a descriptive drawing of an FM converter and inverse model initial LUT.

FIG. 11 is a descriptive drawing of an FM converter and inverse model initial LUT. As illustrated in FIG. 11, a spectral printing converter RC constituting the front end of an FM converter 18 converts the ink amounts Ij of a plurality of types of ink into a spectral reflectivity R(λ) of patches printed in accordance with the ink amounts Ij. In the present embodiment, the printer 20 is assumed to use the four colors of ink described above, and the input of the spectral printing model converter RC, too, is the ink amounts Ij of the four types of ink. However, it is possible to use any desired ink amount Ij as the plurality of types of ink used by the printer 20.

A color calculation unit CC calculates the tint value of the L*a*b* color space from the spectral reflectivity R(λ). A pre-selected light source (for example, a reference light D50) is used as an observational condition of the color chart for calculating the tint value. One method for creating the spectral printing model converter RC which can be employed is the method recited in the publication of Japanese Translation of PCT International Application No. 2007-511175.

The inverse model initial LUT 410 is a look-up table the input of which is an L*a*b* value and the output of which is the ink amount Ij. In the initial LUT 410 for example, the L*a*b* color space is divided into a plurality of small cells, and an optimal ink amount Ij is selected and registered for each of the small cells. This selection is made in consideration of, for example, the image quality of the color chart printed with the ink amount Ij. In general, there exist a plurality of combinations of ink amounts Ij for reproducing a given L*a*b* value. In view whereof, the ink amount Ij selected as being optimal in terms of the image quality or another desired standpoint from among the plurality of combinations of ink amounts Ij for reproducing a substantially identical L*a*b* value is registered in the initial LUT 410. The L*a*b* value, which is the input value of the initial LUT 410, is a representative value of each of the small cells. The ink amount Ij, which is the output value, is intended to reproduce any L*a*b* value in the relevant cell. Accordingly, in the initial LUT 410, the L*a*b*, which is the input value, and the ink amount Ij, which is the output value, are not strictly associated together; and when the ink amount Ij of the output value is converted to the L*a*b* value in the FM converter 18, the resulting value is somewhat different from the input value of the initial LUT 410. The initial LUT 410 employed can also have the input value and output value completely associated together. It is also possible to create the LUT 510 without color correction without the use of the initial LUT 410. One method for selecting the optimal ink amount Ij for each of the small cells and creating the initial LUT 410 which can be employed is, for example, the method recited in the publication of Japanese Translation of PCT International Application No. 2007-511175.

In step S500 of FIG. 10, the forward model (FM) and the duty limiting value of the ink are used to predict the gamut. In step S600, the gamut predicted in step S500 (hereinafter also referred to as the predicted gamut) is evaluated. This determination is performed, for example, by a user. When the evaluation of the predicted gamut is unsatisfactory (a "NO" in S600), the flow returns to step S100.

When the evaluation of the predicted gamut is satisfactory ("YES" in S600), an initial input value is set by the user in step S700 in order to create the LUT 510 without color correction. Values that have been predetermined at substantially equal intervals as each of the RGB values are set as the input values of the LUT 510 without color correction. A group of RGB values is thought of as representing a point in the RGB color space, and therefore, a group of RGB values is also called an "input grid point."

In step S700, the initial values of the ink amounts Ij relative to a plurality of a small number of input grid points that have been pre-selected from among a plurality of input grid points. As the input grid point by which the initial input value is set, preferably, at least the input grid point corresponding to the vertex of a three-dimensional color solid in the RGB color space is selected. At the vertex of the three-dimensional color shape, each of the RGB values takes the minimal value or the maximal value of a defined range thereof. Specifically, in a case where each of the RGB values is expressed in eight bits, the initial input values of the ink amounts Ij are set for eight input grid points, which are (R,G,B)=(0,0,0), (0,0,255), (0,255,0), (255,0,0), (0,255,255), (255,0,255), (255,255,0), and (255,255,255).

In step S800 of FIG. 10, the smoothing processor 15 (FIG. 9) executes a smoothing process (a flattening process) on the basis of the initial input values having been set in step S700.

FIG. 12 is a drawing illustrating the correspondence relationship between an input grid point and the coordinate values of an L*a*b* color space in the smoothing process. FIG. 12B uses double circles and white-filled circles to illustrate the distribution of a plurality of color points in the state prior to the smoothing process. These coordinate values constitute a three-dimensional color solid in the L*a*b* color space. The L*a*b* values of each of the coordinate values are values where the ink amounts Ij at a plurality of input grid points of the LUT 510 without color correction have been converted to L*a*b* values with the FM converter 18. The initial values of the ink amounts Ij for the other input grid points are set by the initial value setting unit 14 (see FIG. 9) from the initial input values.

FIG. 12 illustrates the distribution of color points after the smoothing process. The smoothing process is a process for moving a plurality of coordinate points in the L*a*b* color space to smooth the distribution of the coordinate values to equal intervals. In the smoothing process, the optimal ink amounts Ij for reproducing the L*a*b* values of each of the coordinate values after movement are also decided. At such a time, the optimal ink amounts Ij allocated to the input grid points are calculated on the basis of an objective function E.

Each of the vertices of the three-dimensional color solid CS of the L*a*b* color space (FIGS. 12B and 12C) have a one-to-one correspondence with the vertex of the three-dimensional color solid of the inputted color space (RGB color space) of the LUT 510 without color correction (FIG. 12A). The edges connecting each of the vertices (ridge lines) can also be thought of as being in mutual correspondence in both of the color solids. Each of the coordinate values of the L*a*b* color space prior to the smoothing process (FIG. 12B) are respectively associated with the input grid points of the LUT 510 without color correction; accordingly, each of the color points of the L*a*b* color space after the smoothing process (FIG. 12C) are also respectively associated with the input grid points of the LUT 510 without color correction. The input grid points of the LUT 510 without color correction are not changed by the smoothing process.

When the LUT 510 without color correction is created, the reason for performing the smoothing process in the L*a*b* space is as follows. In the LUT 510 without color correction, it is desirable that ink amounts Ij of the output color space be selected so as to be able to reproduce the greatest possible color region. The color region which can be reproduced with a specific ink set is decided in consideration of the ink duty limiting value (the limiting value of the ink amount Ij that can be discharged onto a certain surface area) and other predetermined limiting conditions. By contrast, the aforesaid forward model FM is created without relation to the color region which can be reproduced, and these limiting conditions are not taken into consideration. In view whereof, during the smoothing process, when the range of coordinate values which can be taken within the L*a*b* space is decided in consideration of the ink duty limiting value and other limiting conditions, it becomes possible to decide the color region which can be reproduced with a specific ink set. The algorithm employed for moving the coordinate values uses, for example, a mechanical model (for an example of a mechanical mode, see Japanese Laid-open Patent Publication 2006-197080).

Figure 13:
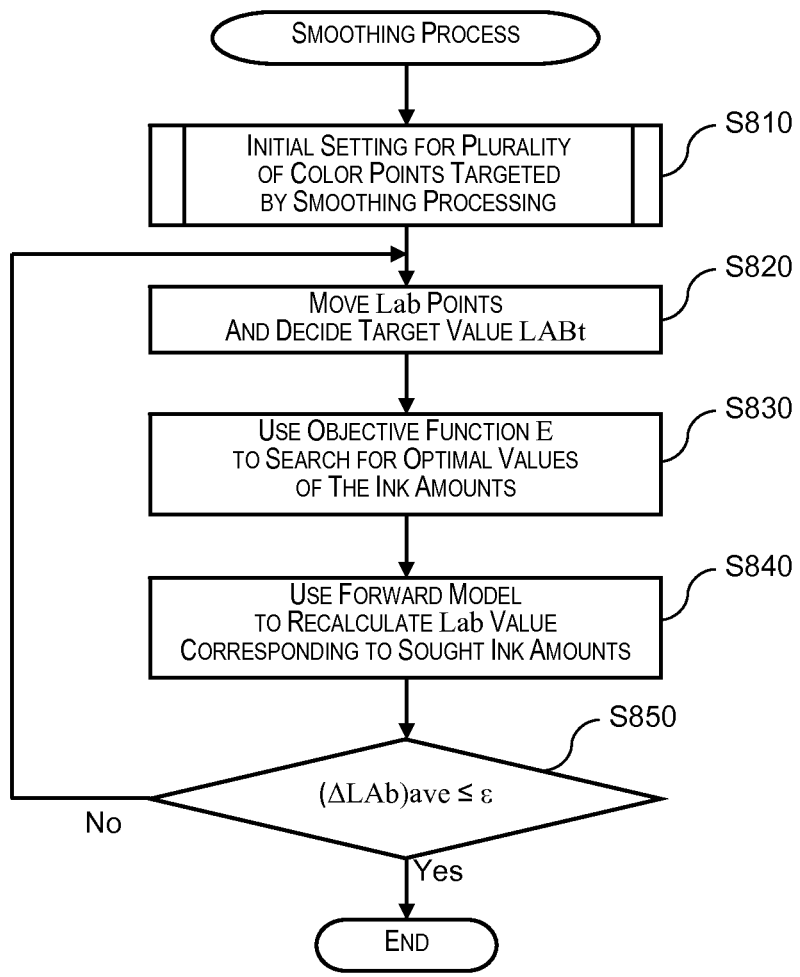
FIG. 13 is a flow diagram illustrating an example of a process sequence in the smoothing process (step S800 of FIG. 10)

FIG. 13 is a flow diagram illustrating an example of a process sequence in the smoothing process (step S800 of FIG. 10). In step S810, the initial value setting unit 14 (FIG. 9) creates an initial setting for the plurality of coordinate values targeted by the smoothing process. Specifically, firstly, a provisional ink amount Ij for each of the coordinate values targeted by the smoothing process is decided from the initial input value of the ink amount Ij. Next, the FM converter 18 is used to determined the L*a*b* value corresponding to the provisional ink amount Ij. Then, the resulting L*a*b* value is again converted to the ink amount Ij with the inverse model initial LUT 410 (FIG. 9).

As a result of the process of step S810, the following initial values are decided for the coordinate values targeted by the smoothing process.

(i) The value of the input grid point of the LUT without color correction: (R, G, B)

(ii) The initial coordinate values of the coordinate values of the L*a*b* color space corresponding to each of the input grid points: L(R,G,B)

(iii) The initial ink amount Ij corresponding to each of the input grid points: I(R,G,B).

As can be understood from the description above, the initial value setting unit 14 has a function for setting an initial value relating to the other input grid points from the input initial value relating to a representative input grid point. The initial value setting unit 14 can also be included in the smoothing processor 15.

In step S820, the smoothing processor 15 moves the coordinate values in the L*a*b* space. FIG. 14 is a descriptive drawing illustrating the process content of steps S820 to S850 in FIG. 13. As illustrated in FIG. 14A, the distribution of coordinate values has a considerable bias prior to the smoothing process. FIG. 14B illustrates the position of each of the color points after a brief period of time has passed. The L*a*b* values after movement are called the "target value LABt." The modifier "target" occurs because the value LABt is used as a target value in the search process for the optimal value of the ink amount Ij as described below.

In step S830, the smoothing processor 15 uses the objective function E represented by the following Formula (6) to search for the optimal ink value Ij for the target value LABt (see FIG. 14C).

[Formula 6]

$$E=|\overrightarrow{LAB_t}-\overrightarrow{LAB_{FM}(Ij)}|^2+\alpha\cdot GI(Ij)+\beta\cdot BI(Ij) \quad (6)$$

Herein, Ij is the ink amount Ij for minimizing the objective function E; LABFM(Ij) is the L*a*b* value obtained from the conversion of the ink amount Ij by the FM converter 18; GI (Ij) is a graininess index of the color chart printed with the ink amount Ij; BI (Ij) is the bronzing index; and α and β are constants. The first item on the right edge of the Formula (6) signifies a computation for determining the square of the distance of the two coordinate values represented by the two vectors LABt, LABFM(Ij).

The aforesaid Formula (6) signifies that the ink amount Ij having a smaller graininess index GI and bronzing index value BI is decided as the optimal ink amount Ij from among the ink amounts Ij for reproducing the L*a*b* values near the coordinate value LABt of the color point after having moved by only very small amounts in the process of step S820. The search for the optimal ink amount Ij is executed with the use of, for example, a quasi-Newton method or other optimization technique. The search for the ink amount Ij is begun from the initial ink values of each of the input grid points having been set in step S810. Accordingly, the ink amount Ij obtained in the search is a value in which the initial ink amount Ij has been revised.

Generally, the search for the ink amount Ij by the optimization process is executed under the following conditions.

(Condition i) Minimizing the objective function E (Condition ii) Using only the ink that has been pre-designated as being available for use Various formulas other than the aforesaid Formula (6) can be employed as the formula for giving the objective function E of condition i. Further, in some cases, only some inks of the plurality of types of inks which can be employed by the printer 20 are designated as the inks available for use in condition ii, and in some cases all the types of inks are designated. The types of inks available for use are preferably pre-set by the user for each of the color points targeted b the smoothing process. A more detailed description of specific examples of these optimization conditions shall be provided below.

Herein, each of the values of the bronzing index value BI recorded in the index value table Ta illustrated in FIG. 8 are acquired. At such a time, the bronzing index value BI (Ij) corresponding to the ink amount Ij is selected in accordance with the category of medium on which the color chart has been formed.

The graininess index GI (Ij) is given by, for example, the following Formula (7).

[Formula 7]

$$GI=a_L\int\sqrt{WS(u)}VTF(u)du \quad (7)$$

Herein, aL is a brightness compensation factor; WS (u) is a Wiener spectrum of the image to be illustrated by the halftone data used for printing the color chart; VTF (u) is a visual spatial frequency characteristic; and u is a spatial frequency characteristic. One method for calculating the graininess index GI is, for example, recited in the publication of Japanese Translation of PCT International Application No. 2007-511161.

In step S840 of FIG. 13, the L*a*b* values corresponding to the ink amounts Ij having been sought in step S830 are again calculated by the FM converter 18 (FIG. 14D). Herein, the reason for recalculating the L*a*b* values is that because the ink amounts Ij having been sought are the ink amounts Ij for minimizing the objective function E, the L*a*b* values reproduced by the ink amounts Ij have shifted somewhat from the target value LABt of the optimization process. In so doing, the recalculated L*a*b* values are used as the coordinate values after the movement of each of the color points.

In step S850, the mean value (ΔLab)ave of the travel of the coordinate values of each of the color points is deemed either to be at or below a pre-set threshold value ε, or not to be. In a case where the mean value (ΔLab)ave of travel is greater than the threshold value ε, then the flow returns to step S820, and the smoothing process of steps S820 to S850 continues. In a case where the mean value (ΔLab)ave of travel is at or below the threshold value ε, then the distribution of color points is thoroughly smooth, and therefore the smoothing process is concluded. The threshold value ε is a suitable value that is empirically decided in advance.

Thus, in the smoothing process (flattening process) of the present embodiment, the optimization technique is used to search for the optimal ink amounts Ij corresponding to the color points after movement while each of the color points are moved each interval in a very short period of time. The process continues until the travel of the color points has become sufficiently small. Consequently, as has been illustrated in FIG. 14C, it is possible to obtain a smooth distribution of color points.

Returning now to FIG. 10, in step S900, the table creation unit 16 uses the results of the smoothing process to create the LUT 510 without color correction. That is, the table creation unit 16 registers, as the output values of the LUT 510 without color correction, the optimal ink amounts Ij for reproducing the color points of the L*a*b* color space having been associated with each of the input grid points. In the smoothing process, in order to reduce the calculation load, it is also possible to select only the color points corresponding to only some of the input grid points of the LUT 510 without color correction to be targeted by the process. For example, in a case where the interval of the RGB values in the input grid points of the LUT 510 without color correction is 16, when the interval of the RGB values in the input grid points targeted by the smoothing process is set to 32, then the load of the smoothing process can be halved. In such a case, the table creation unit 16 decides and registers the ink amounts Ij for all of the input grid points of the LUT 510 without color correction by interpolating the smoothing process results.

In step S1000 of FIG. 10, the LUT 510 without color correction is evaluated. When the evaluation is unsatisfactory ("NO" in S1000), then the flow again returns to step S100. When the evaluation is satisfactory, then the LUT 510 without color correction is registered in the memory unit 12. The LUT creation module uses the LUT 510 without color correction also to create the color correction LUT 610.

Figure 15:
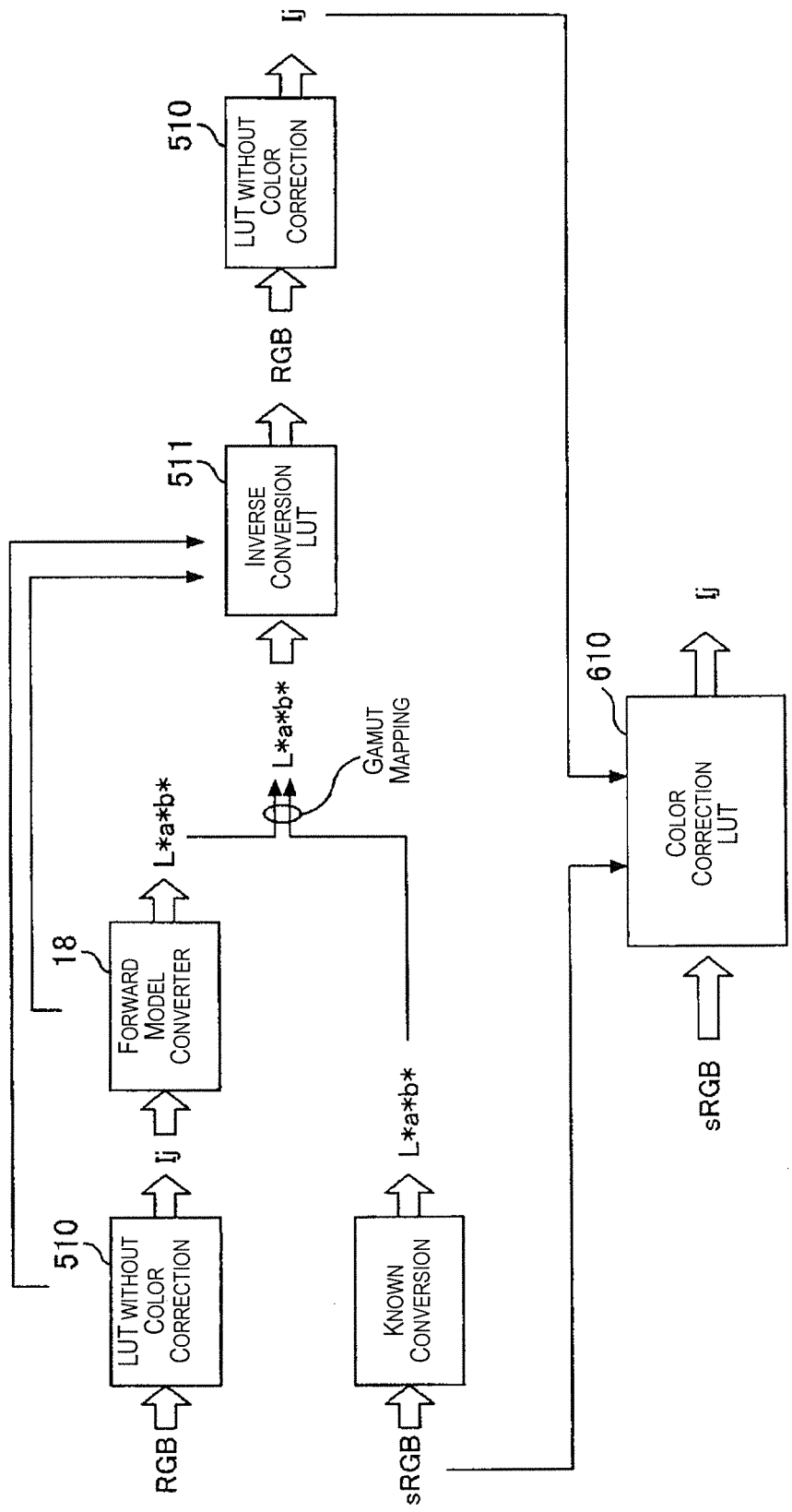
FIG. 15 is a descriptive drawing illustrating a method for creating a color correction LUT using an LUT without color correction.

FIG. 15 is a descriptive drawing illustrating a method for creating the color correction LUT using the LUT without color correction. As described above, the color correction LUT 610 is a look-up table for converting a standard device-dependent color space into the ink amounts Ij for a specific printer, and in the present embodiment, employs an sRGB color space as the device-dependent color space. Hereinafter, as illustrated in FIG. 15, the color correction LUT 610 is created on the basis of the relationship between the ink amounts Ij and the RGB values specified by the LUT without color correction.

Firstly, the RGB values are converted to the ink amounts Ij by the LUT 510 without color correction. The ink amounts Ij after conversion are then converted to the L*a*b* values by the FM converter 18. The sRGB values associated with the color correction LUT 610 are converted to L*a*b* values in accordance with a known conversion equation. The L*a*b* values after conversion are gamut-mapped such that the color region thereof matches the color region of the L*a*b* values having been converted by the FM converter 18.

By contrast, an inverted conversion LUT 511 is created using, as an inverse direction look-up table, the L*a*b* values converted from the RGB values through the LUT 510 without color correction and through the FM converter 18. That is, the inverse conversion LUT 511 is an LUT for creating associations between L*a*b* values and RGB values. Furthermore, the L*a*b* values having been gamut-mapped are converted to RGB values by the inverse conversion LUT 511. The RGB values are again converted to the ink amounts Ij by the LUT 510 without color correction. The associated relationships between the final ink amounts Ij and the initial sRGB values are registered in a look-up table, whereby the color correction LUT 610 is created.

Due to the above, the color correction LUT 610 for creating associations between the color-dependent color space and the ink amounts Ij is created and recorded in the memory unit 12. Thereafter, in the computer 10, the color correction LUT 610 is used to select the ink amounts Ij corresponding to inputted data and output same to the printer 20. In the present embodiment, the bronzing index values BI (Ij) are used as evaluation items for the optimal ink amounts Ij in the creation of the LUT 510 without color correction, which is the origin of the color correction LUT 610. For this reason, a combination of the ink amounts Ij recorded in the color correction LUT 610 is selected so as to inhibit bronzing.

4. Other Embodiments

The use of ink as a recording agent is one example. In a case where, for example, a laser printer is used as the printer 20, then the present index value calculation method can also be applied to a recording agent such as a toner. The use of the LUT creation method as an example of an application of the bronzing index value is one example, and various other examples of applications also exist.

As shall be apparent, the embodiment above is not provided by way of limitation to the invention. Specifically, there can be disclosed, as embodiments of the invention: the applying of mutually interchangeable members, configurations, and the like disclosed in the embodiment above in appropriately altered combinations; the appropriate use, as substitutes, of members, configurations, and the like that have not been disclosed in the embodiment above, but that constitute known art and are mutually interchangeable with the members, configurations, and the like disclosed in the embodiment above, as well as the applying of same in appropriately altered combinations; and the appropriate substituted use of members, configurations, and the like with members, configurations, and the like that have not been disclosed in the embodiment above, but could, on the basis of the known art, be conceived of by a person having ordinary skill in the art as a replacement for the members, configurations, and the like disclosed in the embodiment above, as well as the applying of same in appropriately altered combinations.

The disclosures of Japanese Patent Application No. 2011-081714, filed Apr. 1, 2011 and 2011-132808, filed Jun. 15, 2011 are expressly incorporated in their entirety herein by reference.

What is claimed is:

1. A bronzing index value calculation method, comprising:
    calculating a difference between a hue angle of a colorimetric value of a printed object with respect to diffuse reflection and a hue angle of a colorimetric value of the printed object with respect to specular reflection;
    calculating a difference between a standard chroma with respect to an observational light source and a chroma of a colorimetric value of the printed object with respect to specular reflection under the observational light source; and
    calculating a bronzing index value on the basis of a value obtained by multiplying the calculated difference of the hue angles by the calculated difference of the chromas.

2. The bronzing index value calculation method according to claim 1, wherein
    in calculating the index value, a weighting is set such that the bronzing index value is lower at a lower chroma.

3. The bronzing index value calculation method according to claim 1, wherein
    in calculating the index value, the difference of the hue angles and the difference of the chromas are normalized.

4. The bronzing index value calculation method according to claim 1, wherein the bronzing index value is acquired for individual printed objects.

5. A bronzing index value calculation device, comprising:
    difference calculating means for calculating a difference between a hue angle of a colorimetric value of the printed object with respect to diffuse reflection and a hue angle of a colorimetric value of the printed object with respect to specular reflection;

chroma difference calculating means for calculating the difference between a standard chroma with respect to an observational light source and a chroma of a colorimetric value of the printed object with respect to specular reflection under the observational light source; and index value calculating means for calculating a bronzing index value on the basis of a value obtained by multiplying the calculated difference of the hue angles by the calculated difference of the chromas.

* * * * *